United States Patent [19]
Watanabe et al.

[11] Patent Number: 5,922,873
[45] Date of Patent: Jul. 13, 1999

[54] PROCESS FOR PREPARING N-TERT-BUTYL-2-PYRAZINECARBOXAMIDE AND N-TERT-BUTYL-2-PIPERAZINECARBOXAMIDE

[75] Inventors: Nanao Watanabe; Sadao Asahi; Hideki Kuranishi, all of Osaka, Japan

[73] Assignee: Koei Chemical Co., Ltd., Osaka, Japan

[21] Appl. No.: 09/008,815

[22] Filed: Jan. 20, 1998

Related U.S. Application Data

[62] Division of application No. 08/481,510, filed as application No. PCT/JP94/01972, Nov. 21, 1994., Pat. No. 5,734,055

[30] Foreign Application Priority Data

Nov. 22, 1993 [JP] Japan .................................. 5-315996
Jan. 18, 1994 [JP] Japan .................................. 6-18974

[51] Int. Cl.$^6$ .................................................. C07D 241/04
[52] U.S. Cl. ........................................ 544/390; 544/406
[58] Field of Search ............................................. 544/390

[56] References Cited

U.S. PATENT DOCUMENTS 5,070,090  12/1991  Stokbroekx et al. ............... 514/236.5
5,461,154  10/1995  Jungheim et al. ...................... 544/360
5,463,067  10/1995  Askin et al. ............................ 544/360
5,637,711   6/1997  Askin et al. ............................ 544/374

FOREIGN PATENT DOCUMENTS 122355    10/1984  European Pat. Off. .
63-284171 11/1988  Japan .

OTHER PUBLICATIONS

Modern Synthetic Reactions by Herbert O. House, pp. 1–5 (1965).
Barlin, *The Pyrazines*, pp. 275–279 (1982).
*Organic Syntheses* (John Wiley & Sons, Publishers), col. vol. 5 pp. 73–75 (1973).
Schumacher et al. J. Org. Chem. 54, pp. 2242–2244 (1989).
J. March, *Adv. Org. Chem.*, 4th ed., pp. 970–971 (1992).
European Patent Office, Patent Abstracts of Japan, JP–A–02–218669, Publication Date Aug. 31, 1990.
Marzolph et al CA, vol. 105:190963y, p. 717, 1986, for the correponding Japanese Unexamined Patent Publication No. 151174/1986.
Marzolph et al CA, vol. 107:236524c, p. 771, 1987, for the corresponding Japanewe Unexamined Patent Publication No. 198662/1987, Sep. 2, 1987.
Y. Ito et al., 2–(Aminomethy)piperazine derivatives as intermediates for drugs., Chemical Abstracts, No. 232862w—vol. 111, 1989.
Sato et al., *J. Chem. Soc. Perkins Trans. I.*, pp. 2877–2881 (1991).

*Primary Examiner*—Emily Bernhardt
*Attorney, Agent, or Firm*—Armstrong, Westerman, Hattori, McLeland & Naughton

[57] ABSTRACT

A process for preparing a N-tert-butyl-2-pyrazinecarboxamide having the formula (2):

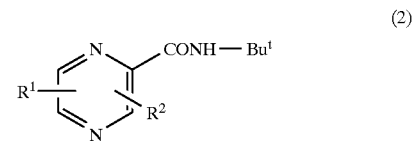

which comprises reacting a cyanopyrazine having the formula (1):

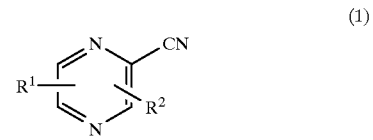

with tert-butyl alcohol in the presence of sulfuric acid and a process for preparing a N-tert-butyl-2-piperazinecarboxamide having the formula (3):

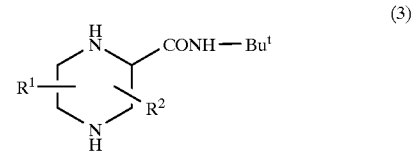

which comprises hydrogenating of said N-tert-butyl-2-pyrazinecarboxamide having the formula (2) in the presence of Raney nickel or Raney cobalt.

5 Claims, No Drawings

PROCESS FOR PREPARING N-TERT-BUTYL-2-PYRAZINECARBOXAMIDE AND N-TERT-BUTYL-2-PIPERAZINECARBOXAMIDE

This is a division of application Ser. No. 08/481,510 filed Jul. 20, 1995, now U.S. Pat. No. 5,734,005 which was a § 371 national phase of international application PCT/JP94/01972 filed Nov. 21, 1994.

TECHNICAL FIELD

The present invention relates to a process for preparing a N-tert-butyl-2-pyrazinecarboxamide and a N-tert-butyl-2-piperazinecarboxamide which are useful as intermediates of medicines.

BACKGROUND OF ARTS

A N-tert-butyl-2-pyrazinecarboxamide is a known compound, and reactions in which this compound is used as a starting substance are already known. There is, however, no report concerning a process for preparing a N-tert-butyl-2-pyrazinecarboxamide.

Also, it is shown in Japanese Unexamined Patent Publication No. 117869/1989 that a N-tert-butyl-2-piperazinecarboxamide, which is one of the compounds obtained by the preparation process of the present invention, can be obtained by hydrogenation of a N-tert-butyl-2-pyrazinecarboxamide.

However, in the above-mentioned process, expensive platinum oxide is used as a catalyst, and the reaction of hydrogenation has to be performed under the high pressure of 100 atm ($1.01 \times 10^4$ kPa) for 6 hours; therefore, the process is not necessarily advantageous for a manufacture on an industrial basis.

An object of the present invention is to obtain a N-tert-butyl-2-pyrazinecarboxamide, which is useful as an intermediate of medicines, in a high yield. The other object of the present invention is to provide a process for preparing a N-tert-butyl-2-piperazine-carboxamide which is useful as an intermediate of medicines by performing hydrogenation of a N-tert-butyl-2-pyrazinecarboxamide under economical and industrially advantageous conditions.

DISCLOSURE OF THE INVENTION

The present inventors had investigated various things to solve the above problems. As a result of the investigation, they found the following facts and completed the present invention: a N-tert-butyl-2-pyrazinecarboxamide can be obtained in a high yield by the reaction of a cyanopyrazine with a tert-butyl alcohol in the presence of sulfuric acid; additionally, a N-tert-butyl-2-piperazinecarboxamide can be prepared in a high yield, unexpectedly under a pressure which is low enough to easily manage for a manufacture on an industrial basis and for a short reaction time, by hydrogenation of the above-mentioned N-tert-butyl-2-pyrazinecarboxamide using inexpensive Raney nickel or Raney cobalt as a catalyst.

Namely, the present invention relates to ① a process for preparing a N-tert-butyl-2-pyrazine-carboxamide having the formula (2):

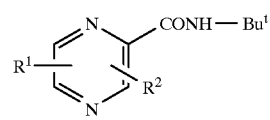

(2)

wherein $R^1$ and $R^2$ are the same or different from each other and each represents an alkyl group or hydrogen; $Bu^t$ represents tert-butyl group, which comprises reacting a cyanopyrazine having the formula (1):

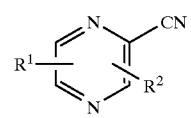

(1)

wherein $R^1$ and $R^2$ are the same as the above, with tert-butyl alcohol in the presence of sulfuric acid; ② a process for preparing a N-tert-butyl-2-piperazine-carboxamide having the formula (3):

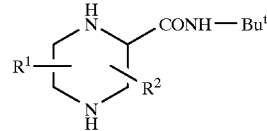

(3)

wherein $R^1$, $R^2$ and $Bu^t$ are the same as the above, which comprises hydrogenating of a N-tert-butyl-2-pyrazinecarboxamide having the formula (2):

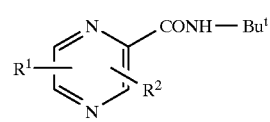

(2)

wherein $R^1$, $R^2$ and $Bu^t$ are the same as the above, in the presence of Raney nickel or Raney cobalt; and ③ a process for preparing a N-tert-butyl-2-piperazine-carboxamide having the formula (3):

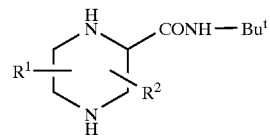

(3)

wherein $R^1$, $R^2$ and $Bu^t$ are the same as the above, which comprises reacting in that a cyanopyrazine having the formula (1):

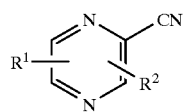

(1)

wherein $R^1$ and $R^2$ are the same as the above, with tert-butyl alcohol in the presence of sulfuric acid to prepare a N-tert-butyl-2-pyrazinecarboxamide having the formula (2):

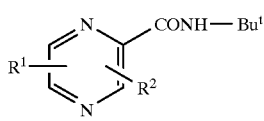

(2)

wherein $R^1$, $R^2$ and $Bu^t$ are the same as the above, and hydrogenating of said N-tert-butyl-2-pyrazinecarboxamide in the presence of Raney nickel or Raney cobalt.

In the above-mentioned processes, it is preferable that 2 to 5 moles of sulfuric acid is used to one mole of a cyanopyrazine having the formula (1), and that the reaction is performed at 0° to 50° C. Further, it is preferable that the above-mentioned hydrogenation is performed at 70° to 130° C.

In order to perform the process of the present invention for preparing a N-tert-butyl-2-pyrazine-carboxamide having the formula (2), tert-butyl alcohol may be added dropwise to the mixture of sulfuric acid and a cyanopyrazine having the formula (1), or, contrary to the above, the cyanopyrazine may be added dropwise to the mixture of sulfuric acid and tert-butyl alcohol (Reaction 1).

In a cyanopyrazine having the formula (1) (hereinafter referred to as "a cyanopyrazine (1)"), the substituents $R^1$ and $R^2$ are the same or different from each other, and each represents an alkyl group or hydrogen. Examples of the alkyl group are lower alkyl groups having 1 to 4 carbon atoms such as methyl, ethyl propyl, isopropyl, butyl and isobutyl.

Examples of the cyanopyrazine having the formula (1) are 2-cyanopyrazine, 3-, 5- or 6-methyl-2-cyanopyrazine, 3-, 5- or 6-ethyl-2-cyanopyrazine, 3-, 5- or 6-(iso)propyl-2-cyanopyrazine, 3-, 5- or 6-(iso)butyl-2-cyanopyrazine, 3,5-dimethyl-2-cyanopyrazine, 5,6-dimethyl-2-cyanopyrazine and the like.

An example of the preparation process by Reaction 1 is as follows. At first, a cyanopyrazine (1) is added dropwise to sulfuric acid to prepare a sulfuric acid solution of a cyanopyrazine (1). Here, 50 to 100% (percentage by weight, hereinafter the same) of sulfuric acid may be used, and it is preferable that 70 to 90% aqueous solution of sulfuric acid is used. An amount of sulfuric acid used to one mole of a cyanopyrazine (1) is at least 2 moles, preferably 2 to 5 moles, more preferably 3.3 to 5 moles. These amounts are adequate to obtain the intended product in a high yield. In case that an amount of sulfuric acid used to one mole of a cyanopyrazine (1) is less than 2 moles, the yield decreases.

Then, tert-butyl alcohol is added dropwise to thus prepared sulfuric acid solution of a cyanopyrazine (1) with stirring to perform a reaction. An amount of tert-butyl alcohol used to one mole of a cyanopyrazine (1) is at least one mole, and, from an economical point of view, 1 mole to about 2 moles are appropriate. The reaction can be performed at the temperature of 0° to 90° C., however, in order to attain a high yield, the lower temperature is preferable. The preferable reaction temperature is 0° to 50° C., more preferably 0° to 20 C. Tert-butyl alcohol is added dropwise over 0.5 to 5 hours and, then, kept at the same temperature for 0 to 10 hours to complete the reaction. Concerning the reaction pressure, atmospheric pressure is sufficient.

After the reaction is completed, the product can be isolated from the reaction liquid in the following manner. The reaction liquid is added to water, or water is added to the reaction liquid. Then, an alkali such as sodium hydroxide, potassium hydroxide or ammonia is added to the mixture to neutralize it. The precipitated crystalline solid is separated by filtration, washed with water and dried. Then, a N-tert-butyl-2-pyrazine carboxamide having the formula (2) (hereinafter referred to as "N-tert-butyl-2-pyrazinecarboxamide (2)") can be obtained.

Besides, the preparation process by the above-mentioned Reaction 1, a process using isobutylene instead of tert-butyl alcohol was investigated as another process, however, a N-tert-butyl-2-pyrazinecarboxamide was obtained only in a low yield as shown below in Reference Example.

Thus obtained N-tert-butyl-2-pyrazinecarboxamide (2) is available for hydrogenation (Reaction 2) in the preparation process of the present invention, after drying it or as it is in the condition containing moisture after the washing process without drying.

In a N-tert-butyl-2-pyrazinecarboxamide having the formula (2), the substituents $R^1$ and $R^2$ are the same or different from each other, and each represents an alkyl group or hydrogen. Examples of the alkyl group are lower alkyl groups having 1 to 4 carbon atoms such as methyl, ethyl, propyl, isopropyl, butyl and isobutyl.

Examples of the N-tert-butyl-2-pyrazine-carboxamide having the formula (2) are N-tert-butyl-2-pyrazinecarboxamide, N-tert-butyl-3,5 or 6-methyl-2-pyrazinecarboxamide, N-tert-butyl-3,5 or 6-ethyl-2-pyrazinecarboxamide, N-tert-butyl-3,5, 3,6 or 5,6-dimethyl-2-pyrazinecarboxamide and the like.

A N-tert-butyl-2-pyrazinecarboxamide having the formula (2) of which $R^2$ is hydrogen and locates at the 3-position can also be prepared by decarboxylation in which a compound having the formula (4):

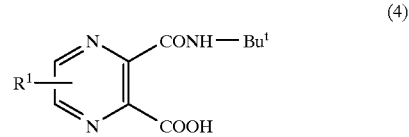

(4)

wherein $R^1$ represents alkyl group or hydrogen; $Bu^t$ is the same as the above, is heated.

A compound having the formula (4) can be obtained as follows. The corresponding 2,3-dicyano-pyrazine is reacted with tert-butyl alcohol or isobutylene in the presence of sulfuric acid to obtain the corresponding N-tert-butyl-2-pyrazinecarboxamide and/or 3-cyano-N-tert-butyl-2-pyrazinecarboxamide. Then, thus obtained corresponding N-tert-butyl-2-pyrazinecarboxamide and/or 3-cyano-N-tert-butyl-2-pyrazinecarboxamide are hydrolyzed under an alkaline condition.

The hydrogenation of Reaction 2 in the preparation process of the present invention is usually performed as follows. An autoclave is charged with a N-tert-butyl-2-pyrazinecarboxamide (2), Raney nickel or Raney cobalt and a solvent. The mixture is heated to 50°–150° C. and stirred under a pressure of 50 atm ($5.1 \times 10^3$ kPa) or less, preferably 10 to 50 atm ($1.0 \times 10^3$ to $5.1 \times 10^3$ kPa) with introducing hydrogen thereto. The absorbance of hydrogen is finished 1 to 5 hours later, and the reaction is completed to produce a N-tert-butyl-2-piperazinecarboxamide having the formula (3) (hereinafter referred to as "N-tert-butyl-2-piperazinecarboxamide (3)") in a high yield. It is not preferable that the reaction temperature is lower than the above scope, because the reaction does not proceed well and needs longer time therefor. It is not preferable either that the reaction temperature is higher than the above scope, because side reactions increase and the yield of an intended product decreases.

Preferably, when the hydrogenation is performed at 70° to 130° C. to complete Reaction 2, an intended product N-tert-butyl-2-piperazinecarboxamide (3) can be almost quantitatively produced.

Concerning an amount of the catalyst used, Raney nickel or Raney cobalt, the more it is used the more preferable because the more it is used, the less the reaction time is. From the economical point of view, however, it is preferable that 1 to 30% by weight of the catalyst based on the amount of N-tert-butyl-2-pyrazinecarboxamide (2) is used.

The solvent used in the present reaction is not especially limited, if it can dissolve a N-tert-butyl-2-pyrazinecarboxamide (2) and the solvent itself is not hydrogenated. Examples thereof are water, methanol, ethanol, 2-propanol, n-butyl alcohol, a mixture thereof and the like.

After the reaction is completed, the reaction liquid is cooled, and the catalyst is filtered off and then the solvent is distilled away, so that the intended product is isolated and purified. Since the intended product is produced in a high yield, a highly pure N-tert-butyl-2-piperazinecarboxamide (3) can be obtained only through the above-mentioned steps. Additionally, if recrystallization is performed using a solvent such as methanol, ethanol, 2-propanol, n-butanol or N,N-dimethylformamide, a purer product can be obtained.

BEST MODE FOR CARRYING OUT THE INVENTION

The present invention is explained by means of the following Examples. The present invention is not limited by these Examples.

EXAMPLE 1

To 1030 g of an 80% aqueous solution of sulfuric acid (8.40 moles of sulfuric acid), 220.5 g (2.10 moles) of 2-cyanopyrazine was added dropwise keeping the internal temperature at 40° C. or less with stirring. In succession, 187 g (2.52 moles) of tert-butyl alcohol was added dropwise to the mixture, keeping the internal temperature at 9° to 15° C., over 3 hours. Further, the temperature was kept at the same temperature for 2.5 hours. After the reaction, the reaction liquid was added to 3500 g of water with stirring. Thus obtained mixture was neutralized with an aqueous solution of sodium hydroxide. Precipitated crystalline solid was separated by filtration, washed with water and then dried to obtain 338.7 g (1.89 moles) of N-tert-butyl-2-pyrazine-carboxamide. It had a melting point of 88° to 90° C. Further, from the water layer, from which the intended product had been separated by filtration, 7.17 g (0.04 mole) of the intended product was further obtained by extraction thereof with toluene. Therefore, the yield of N-tert-butyl-2-pyrazinecarboxamide obtained here was 91.9%.

EXAMPLE 2

The procedure which was the same as in Example 1 except the followings was performed: an 80% aqueous solution of sulfuric acid corresponding to 3 moles of sulfuric acid was used to one mole of 2-cyanopyrazirle, and the reaction temperature was 21° to 23° C. N-tert-butyl-2-pyrazinecarboxamide was obtained here in a yield of 78.2%.

EXAMPLE 3

The procedure which was the same as in Example 1 except the followings was performed: an 80% aqueous solution of sulfuric acid corresponding to 2.5 moles of sulfuric acid was used to one mole of 2-cyanopyrazine, and the reaction temperature was 21° to 24° C. N-tert-butyl-2-pyrazinecarboxamide was obtained here in a yield of 73.6%.

REFERENCE EXAMPLE 1

A reaction vessel was charged with 150 g of an 80% aqueous solution of sulfuric acid (1.22 moles of sulfuric acid), 31.5 g of 2-cyanopyrazine (0.30 mole) and 71 g of acetic acid. To the above mixture, 16.5 g (0.29 mole) of isobutylene was added keeping the internal temperature at 20° to 40° C. with stirring over 8 hours to perform a reaction. After the reaction, a part of the reaction liquid was taken as a sample and diluted with methanol. Then, the diluted sample to which an internal standard substance (p-nitrobenzoic acid) was added was subjected to liquid chromatography [column: (Shiseido KAPCELL) C18 S-5, $\phi$ 4.0 mm×25 cm (made by Shiseido Co., Ltd.), eluate: methanol/water=50/50 (ratio by volume, provided that the water was adjusted to pH 3.5 with a buffer), flow rate of eluate: 0.5 ml/min, temperature: 50° C., detected wavelength: 220 nm] to be quantitatively determined. A yield of N-tert-butyl-2-pyrazine-carboxamide was 44%.

REFERENCE EXAMPLE 2

To 150 g of an 80% aqueous solution of sulfuric acid (1.22 moles of sulfuric acid) of which temperature was kept at 0° to 5° C., 69.6 g (1.24 moles) of isobutylene was introduced with stirring over 3 hours. Then, 64.9 g (0.62 mole) of 2-cyanopyrazine was added dropwise over 0.7 hour to the mixture of which temperature was kept at 5° to 30° C. Further, the mixture was kept at 30° C. for 3 hours. The quantitative determination of the product was performed in the same way as Reference Example 1. A yield of N-tert-butyl-2-pyrazinecarboxamide was 44%.

EXAMPLE 4

An autoclave was charged with 100 g (0.56 mole) of N-tert-butyl-2-pyrazinecarboxamide, 20 g of Raney nickel and 130 g of methanol. The mixture was heated up to 100° C. with stirring and with introducing hydrogen thereto. Kept at the same temperature, the introduction of hydrogen was continued at a reaction pressure of 40 atm ($4.1 \times 10^3$ kPa) for 1 hour, so that the reaction completed. After the reaction completed, the reaction liquid was cooled to room temperature, and Raney nickel was removed by filtration. Then, methanol was distilled away from the filtrate using an evaporator to obtain 103 g of crystalline solid. According to the result of an analysis by gas chromatography (column: G-100, $\phi$ 1.2 mm×40 m (made by Chemicals Inspection & Testing Institute, Japan), carrier gas: He, flow rate of carrier gas: 25 mg /min, temperature of column: raised at the rate of 10° C. /min from 120° C. to 230° C.), the obtained crystalline solid was N-tert-butyl-2-piperazinecarboxamide having 97.3% of purity. The yield was 96.6%.

EXAMPLE 5

The procedure which was the same as in Example 4 except that 20 g of Raney cobalt was used in stead of Raney nickel was performed to obtain 103 g of crystalline solid. The crystalline solid was analyzed in the same way as the above by gas chromatography, and it was found that the crystalline solid was N-tert-butyl-2-piperazine-carboxamide having 99.2% of purity. The yield was 98.5%.

EXAMPLE 6

The procedure which was the same as in Example 4 except the following was performed: an autoclave was charged with 100 g (0.56 mole) of N-tert-butyl-2-pyrazine-carboxamide, 10 g of Raney cobalt and 200 g of a mixed solvent of water and methanol (1/1 ratio by weight) and the mixture was heated up to 110° C. with stirring and with introducing hydrogen thereto, and methanol and water were distilled away from the filtrate using an evaporator. Crystalline solid (103 g) was obtained. The crystalline solid was analyzed in the same way as the above by gas chromatography, and it was found that the crystalline solid was N-tert-butyl-2-pyperazinecarboxamide having 97.5% of purity. The yield was 96.8%.

EXAMPLE 7

To 1030 g of an 80% aqueous solution of sulfuric acid (8.40 moles of sulfuric acid), 220.5 g (2.1.0 moles) of 2-cyanopyrazine was added dropwise keeping the internal temperature at 40° C. or less with stirring. In succession, 187 g (2.52 moles) of tert-butyl alcohol was added dropwise to the mixture of which internal temperature was kept at 9° to 15° C. over 3 hours. Further, the temperature was kept at the same temperature for 2.5 hours. After that, the reaction liquid was poured into 3500 g of water with stirring. Thus obtained mixture was neutralized with an aqueous solution of sodium hydroxide. The precipitated crystalline solid was separated by filtration, washed with water and dried to obtain 338.7 g (1.89 moles) of N-tert-butyl-2-pyrazinecarboxamide. It had a melting point of 88° to 90° C. Further, from the filtrate 7.17 g (0.04 mole) of N-tert-butyl-2-pyrazine-carboxamide was further obtained by extraction thereof with toluene. The yield thereof was 91.9%.

The procedure which was the same as in Example 5 except that 130 g of thus obtained wet N-tert-butyl-2-pyrazinecarboxamide before drying (containing 30 g of water) was used, was performed to obtain the same result as in Example 5, N-tert-butyl-2-piperazinecarboxamide in a yield of 98.5%.

INDUSTRIAL AVAILABILITY

According to the present invention, by reacting a cyanopyrazine (1) with tert-butyl alcohol in the presence of sulfuric acid, a N-tert-butyl-pyrazinecarboxamide (2) which is useful as an intermediate of medicines can be prepared in a high yield. Further, by hydrogenation of N-tert-butyl-2-pyrazine-carboxamide (2) using inexpensive Raney nickel or Raney cobalt as a catalyst, a N-tert-butyl-2-piperazine-carboxamide (3) which is useful as an intermediate of medicines, with the reaction of short time under low pressure can be prepared in a high yield. The preparation process of the present invention is excellent as a process for commercially preparing the above-mentioned substances (2) and (3).

We claim:

1. A process for preparing a N-tert-butyl-2-piperazinecarboxamide having the formula (3):

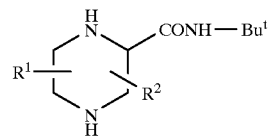

wherein $R^1$, $R^2$ are the same or different from each other and each represents an alkyl group or hydrogen, and $Bu^t$ represents tert-butyl group, which comprises hydrogenating a N-tert-butyl-2-pyrazinecarboxamide having the formula (2):

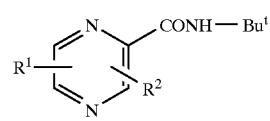

wherein $R^1$, $R^2$ and $Bu^t$ are the same as the above, in the presence of Raney cobalt.

2. A process for preparing a N-tert-butyl-2-piperazinecarboxamide having the formula (3):

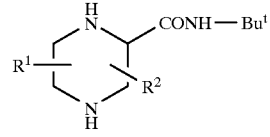

wherein $R^1$, $R^2$ are the same or different from each other and each represents an alkyl group or hydrogen, $Bu^t$ represents tert-butyl group, which comprises reacting a cyanopyrazine having the formula (1):

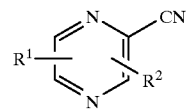

wherein $R^1$ and $R^2$ are the same as the above, with tert-butyl alcohol in the presence of at least 2 moles of sulfuric acid to one mole of said cyanopyrazine (1) at a temperature of 0° C. to 50° C. to prepare a N-tert-butyl-2-pyrazinecarboxamide having the formula (2):

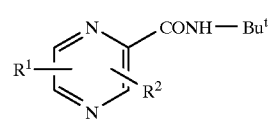

wherein $R^1$, $R^2$ and $Bu^t$ are the same as the above, and hydrogenating said N-tert-butyl-2-pyrazinecarboxamide in the presence of Raney nickel or Raney cobalt.

3. The process of claim 2, wherein 2 to 5 moles of sulfuric acid is used to one mole of a cyanopyrazine having the formula (1).

4. The process of claim 1, wherein the hydrogenation is performed at 70° to 130° C.

5. The process of claim 2, wherein the hydrogenation is performed at 70° C. to 130° C.

* * * * *